Figure 1:
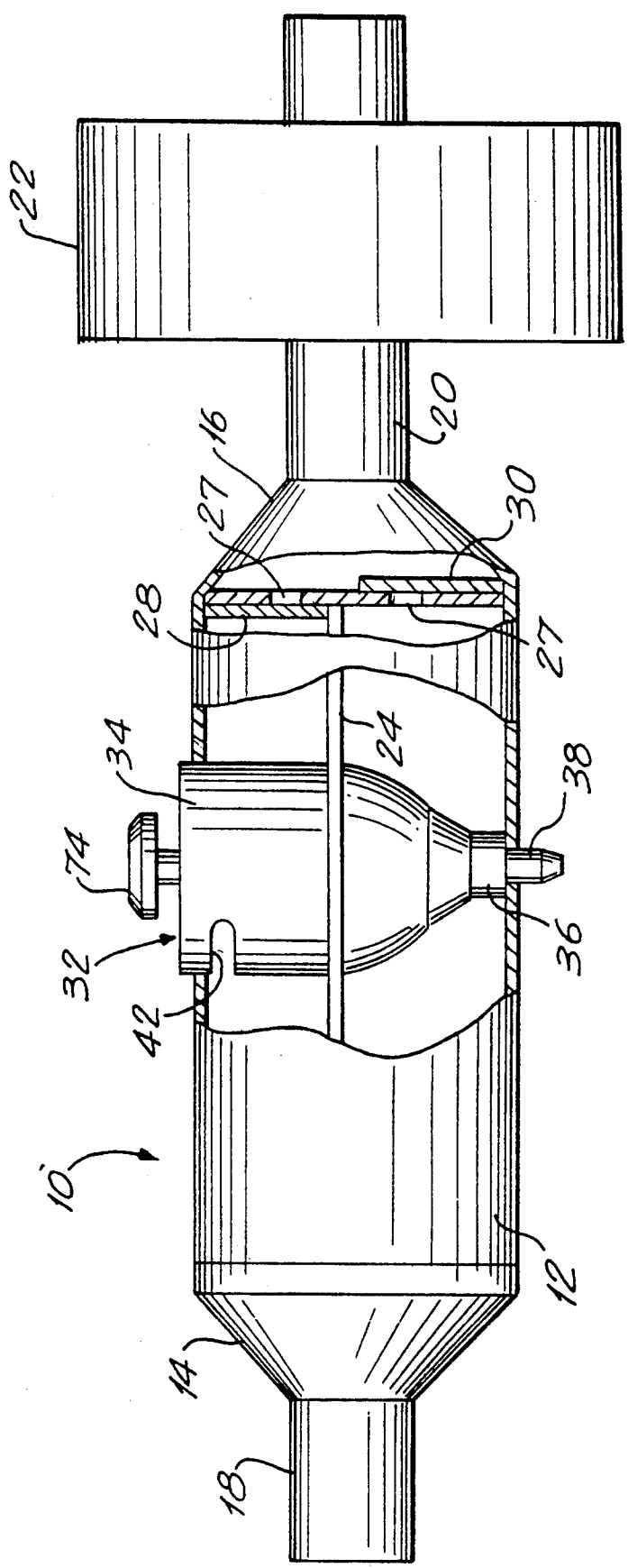
Figure 3:
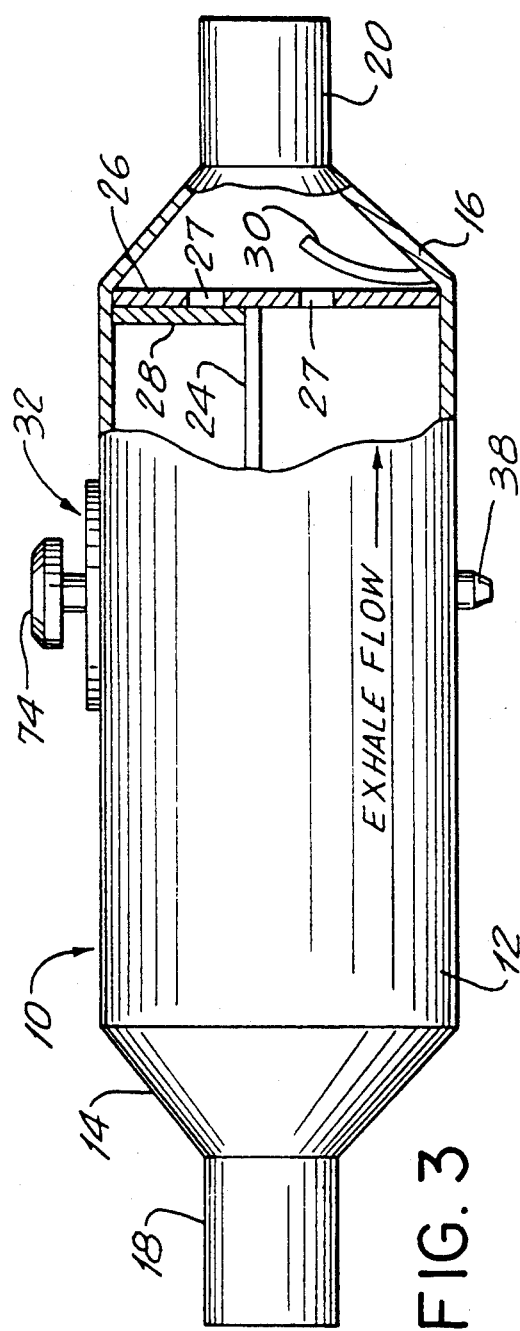
Figure 2:
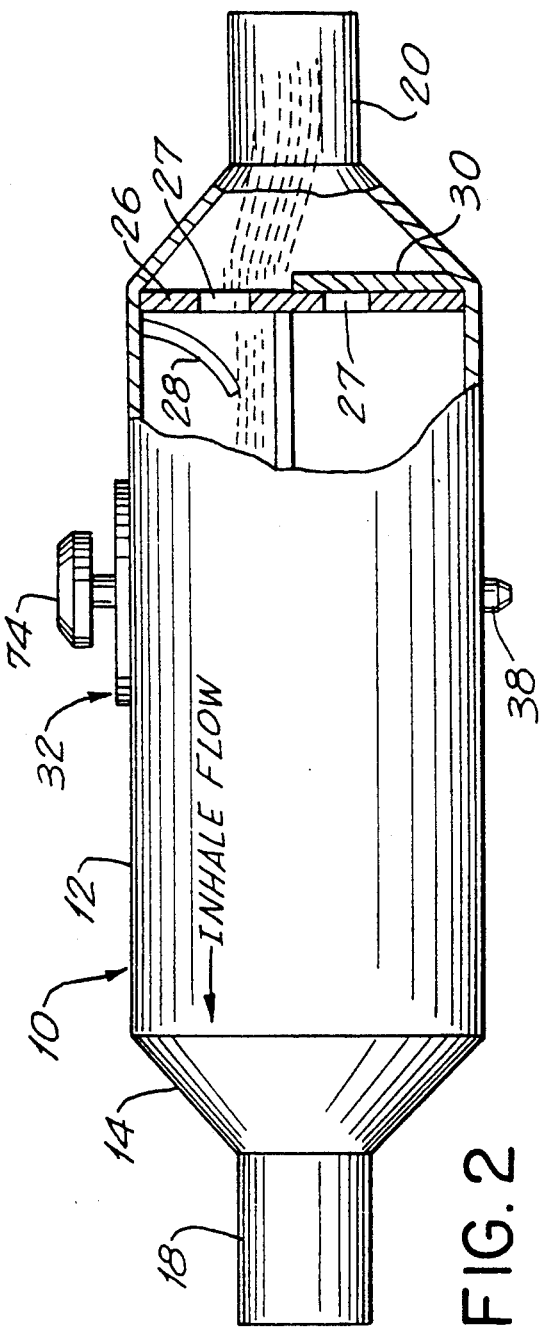
Figure 4:
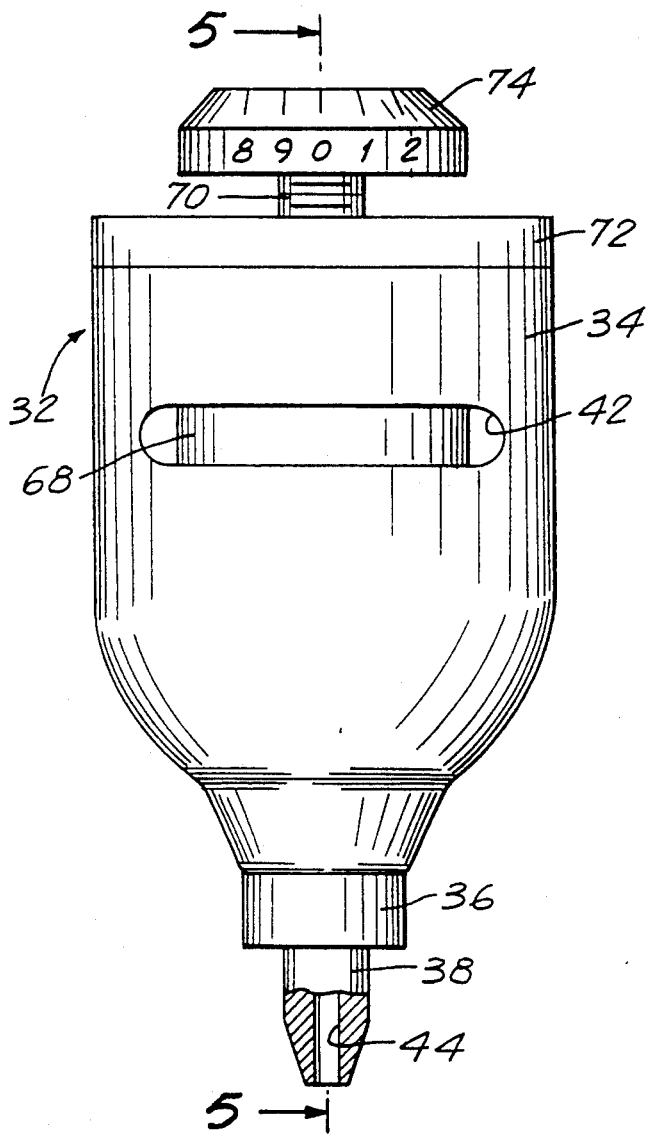

United States Patent [19]

Small, Jr.

[11] Patent Number: 5,165,392

[45] Date of Patent: Nov. 24, 1992

[54] ACCUVENT AEROSOL DELIVERY SYSTEM

[76] Inventor: John C. Small, Jr., 232 Lakes Rd., Bethlehem, Conn. 06751

[21] Appl. No.: 731,037

[22] Filed: Jul. 16, 1991

[51] Int. Cl.$^5$ ............................................. A61M 11/00
[52] U.S. Cl. ............................. 128/200.18; 128/200.21
[58] Field of Search ...................... 128/200.14, 200.18, 128/200.21, 911; 251/321

[56] References Cited

U.S. PATENT DOCUMENTS

| | | | |
|---|---|---|---|
| 2,723,055 | 11/1955 | Beard | 251/321 |
| 2,826,454 | 3/1958 | Coanda | 128/200.18 |
| 3,580,249 | 5/1971 | Takaoka | 128/194 |
| 3,591,090 | 7/1971 | Carden | 239/305 |
| 3,744,722 | 7/1973 | Burns | 239/338 |
| 3,838,686 | 10/1974 | Szekely | 128/173 |
| 4,333,450 | 6/1982 | Lester | 128/200.14 |
| 4,454,877 | 6/1984 | Miller et al. | 128/200.21 |
| 4,512,341 | 4/1985 | Lester | 128/200.21 |
| 4,529,003 | 7/1985 | Iannuzzelli et al. | 128/200.14 |
| 4,560,519 | 12/1985 | Cerny | 261/78 A |
| 4,566,452 | 1/1986 | Farr | 128/200.21 |
| 4,588,129 | 5/1986 | Shanks | 239/338 |
| 4,598,704 | 7/1986 | Bordoni et al. | 128/200.14 |
| 4,657,007 | 4/1987 | Cartin et al. | 128/200.18 |
| 4,703,753 | 11/1987 | Bordoni et al. | 128/200.14 |
| 4,792,097 | 12/1988 | Kremer et al. | 239/338 |
| 4,886,055 | 12/1989 | Hoppough | 128/200.14 |
| 4,907,581 | 3/1990 | King | 128/200.18 |
| 5,054,477 | 10/1991 | Terada et al. | 128/200.14 |

Primary Examiner—Clifford D. Crowder
Assistant Examiner—Stephen R. Funk
Attorney, Agent, or Firm—Schweitzer Cornman & Gross

[57] ABSTRACT

A nebulizer manifold has upper and lower, vertically juxtaposed, chambers which have respective check valves enabling the ingress only and the egress only of air from the associated ends of the respective chambers. A nebulizer injects its mist output into the fluid flow in the chamber permitting only the ingress of fresh air past a check valve, to create medicated air for inhaling by a patient. The other chamber receives exhaled air and allows it to flow outwards away from the patient and to suitable biological filters. The nebulizer provides for aspiration of a liquid to a movable plate orifice to allow a fluid jet stream to entrain the liquid and then strike a boss movable with the plate to form a mist. Control of the rate at which medication is being received is effected by moving the orifice plate to alter the amount of aspirated liquid supplied to the jet stream.

5 Claims, 4 Drawing Sheets

ACCUVENT AEROSOL DELIVERY SYSTEM

INTRODUCTION

1. Field of the Invention

This invention relates to nebulizer systems, and more particularly to an improved nebulizer of compact design contained in a unique, compact manifold delivery system.

2. Prior Art

Nebulizers are well known. They are instruments for providing a misty or nebulous fluid which may be a medication used in applications of disease prophylaxis and therapy or a radioactive pharmaceutical for use in ventilation scans and for other nuclear medicine applications.

U.S. Pat. Nos. directed to nebulizers include Takaoka (3,580,249); Carden (3,591,090); Burns (3,744,722); Szekely (3,838,686); Lester (1) (4,333,450); Lester (2) (4,512,341); Miller et al (4,454,877); Cerny (4,560,519); Farr (4,566,452); Shanks (4,588,129); Bordoni et al (1) (4,598,704); Carlin et al (4,657,007); Bordoni et al (2) (4,703,753); Kremer et al (4,792,097); and Hoppough (4,886,055). Takaoka shows a nebulizer using a venturi tube. Carden shows a nebulizer having two liquid reservoirs. Burns shows a nebulizer in which the target for a gas jet entraining liquid produces uniformly sized particles. Szekely shows a nebulizer wherein the target is a baffle. Lester (1) shows a nebulizer wherein the nebulizer has a diaphragm controlling the exhaust port. Lester (2) shows a nebulizer wherein action occurs regardless of its orientation. Miller et al show a portable nebulizer that regulates moisture content of the air. Cerny shows a self-contained nebulizer system employing a baffle to restrict oversized particles. Farr shows a nebulizer system which uses substantially all of the medication. Shanks shows a nebulizer having a convex target system. Bordoni et al (1) show a radioactive medication nebulizer. Carlin et al show a nebulizer that the patient can easily block the flow of gas in to regulate it. Bardoni et al (2) show a radioactive aerosol device employing disposable pulmonary inhalation devices. Kremer et al show a non-sputtering nebulizer. Hoppough shows a nebulizer having an atmosphere adjusted collar.

SUMMARY OF THE INVENTION

It is an object of this invention to provide a more efficient and effective nebulizer of compact design.

It is a further object of the invention to provide a nebulizer which provides more accurate dosages than heretofore possible.

It is another object of the invention to provide a nebulizer which provides for more comfortable delivery of irritating medication.

It is a still further object of the invention to provide a nebulizer which requires less medication to achieve the same delivery to a patient.

Another object of the invention is to provide a nebulizer which causes less aeration and foaming of the medication than heretofore possible.

It is an additional object of the invention to provide a nebulizer having simple component designs which facilitate component manufacture by inexpensive injection molding techniques.

The objects of the invention are achieved through a manifold system having a unitary hollow body with a first opening to accommodate the ingress of fresh air and the egress of exhaled air, and a second opening to accommodate the egress of modified fresh air and the ingress of exhaled air. The two openings are interconnected by each of two vertically juxtaposed chambers in the hollow body. One chamber is valved to pass fresh air from the first opening to the second opening, and the second chamber is valved to pass exhaled air from the second opening to the first opening and at a distance from the user. The manifold seats a nebulizer having an outlet in the downstream side of the first chamber to pass mist therethrough. Fresh air will be modified by the nebulizer as it is inhaled through the first chamber of the manifold and past the nebulizer therein, by the user patient. Air exhaled by the user patient will pass through the other chamber, the nebulizer not significantly obstructing it either.

The nebulizer is of a new design producing an aerosol of unusually fine particles. In addition, it is incrementally adjustable to vary the number of fine particles being produced.

The nebulizer includes a stem active to pass a jet of pressurized gas such as air or oxygen, out of its upper flat end or surface and aspirate liquid thereabouts and then through an orifice in a vertically movable flat plate, to where it impinges on the lower round end or surface of a boss at a fixed distance from the plate but movable therewith. The round end of the boss abets the upcoming jet stream to nebulize any entrained liquid particles therein.

Incremental adjustment of the amount of nebulizer misting is obtained by varying the distance of the orifice plate from the flat upper end of the jet stem to adjust the amount of liquid being aspirated to the orifice, thus acting like a positive valve. Aspiration flow to the region between the flat end of the jet stem and the orifice plate is enabled by a sleeve which depends from the orifice plate and encircles the gas stem, the distance between the exterior surface of the jet stem and the interior surface of the depending sleeve being such as to facilitate upward liquid action in amounts the system is designed for. The liquid subjected to upward liquid action will be that placed in the bottom of the nebulizer.

Adjustment of the output of the nebulizer is effected through an index knob fixed to a screw threaded in the lid of the nebulizer which projects above the manifold. The lower end of the screw reacts against the upper side of a biased boss plate, moving it down against the bias or allowing it to follow it upwards. The boss plate is biased against the screw by a spring working indirectly on it through the orifice plate which has an upstanding tubular portion which engages the underside of the boss plate. The upwardly extending tubular portion of the orifice plate has cut-away portions to allow the egress of the mist being created within the volume defined by the orifice plate and its upstanding tubular portion and the boss plate. The egressing mist flows down along side of the outside of the orifice-plate upstanding portion and the inside of an encompassing tubular portion depending downwards from the boss plate. The aerosol mist then moves out of the nebulizer through the nebulizer outlet to mix with fresh air and move down the upper manifold chamber to the user.

A feature of the invention is that its compactness results in a light nebulizer which is easily handled by a patient. This enables the lengthy hoses previously used for connecting a heavy manifold with the patient, to be shortened or eliminated. This in turn allows for delivery of more precise or accurate dosages to the patient, as less may be left in the transport path.

A further advantage is that, because of the efficient size of the medication chamber in the nebulizer, less medication is wasted, resulting in additional economies.

Another feature of the invention is that the precise valving of the nebulizer minimizes the amount of medicated air being recirculated in the nebulizer, and hence reduces frothing and foaming.

The openings at the ends of the manifold are formed in tubular members which permit the attachment of hoses or tubing should such be necessary for certain applications, or the direct attachment of a mouthpiece. The tubing at the outlet end of the manifold facilitates the attachment of standard biological filters.

Figure 6:
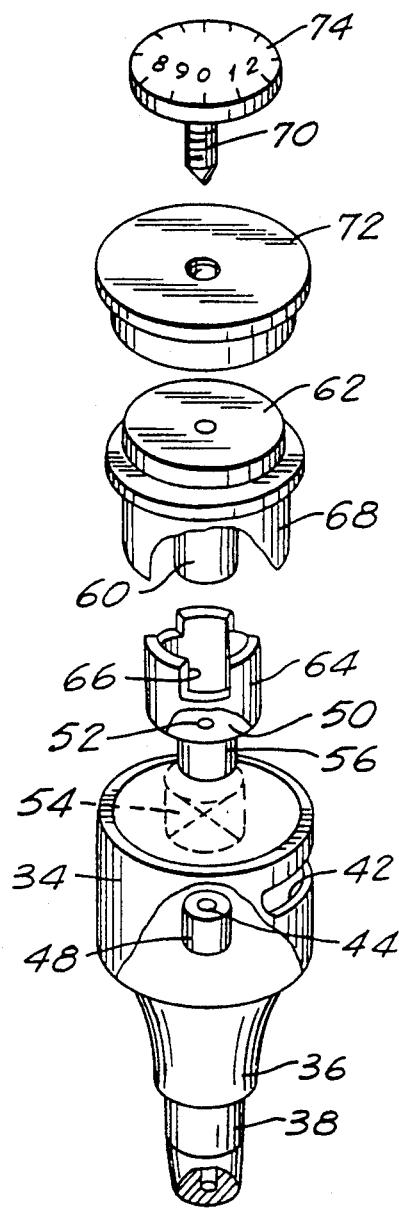
Figure 5:
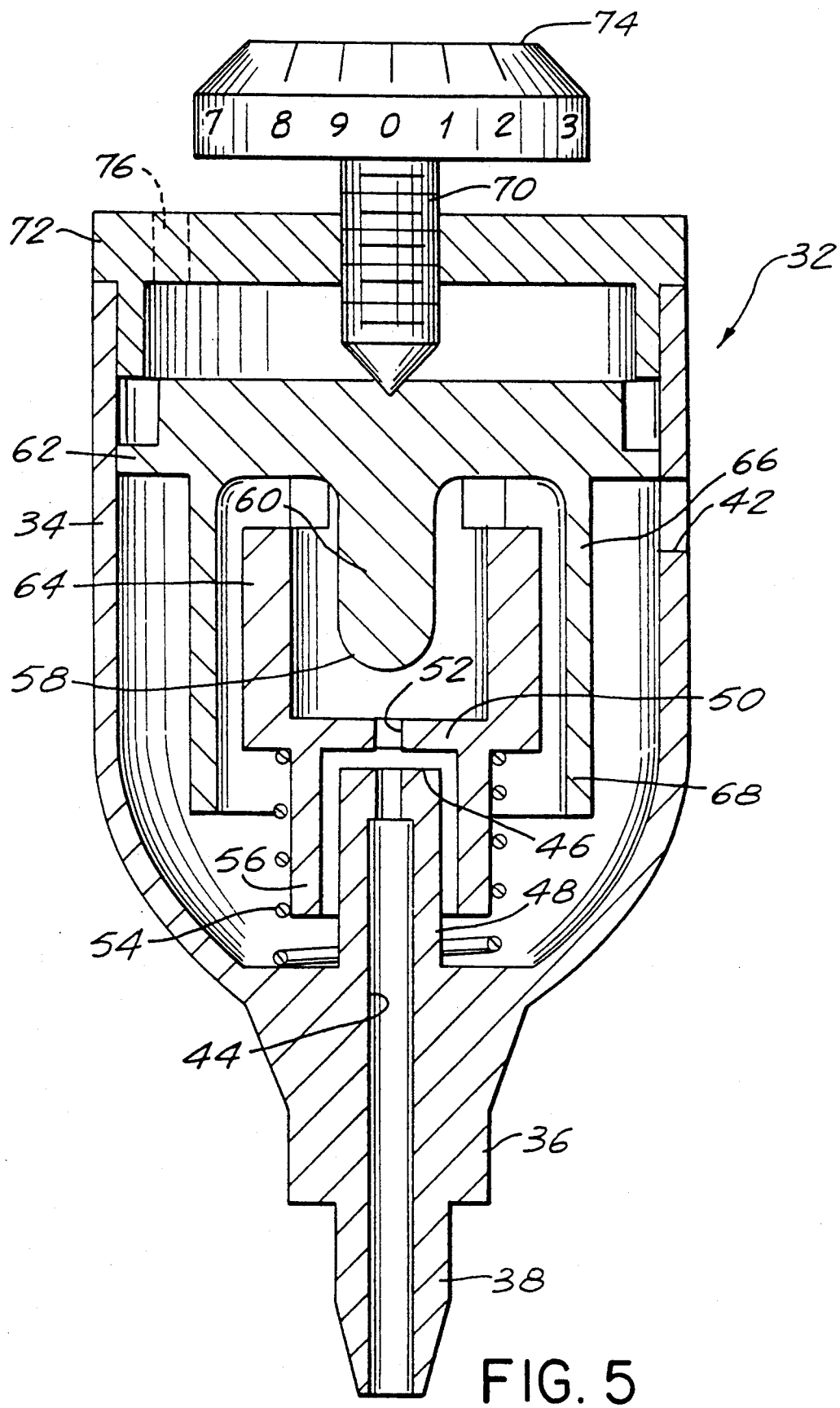

An advantage of the invention is that variable delivery rates provided by the nebulizer, enable the physician to select the least uncomfortable delivery rate of irritating medicines: the rate of delivery can be reduced or increased to tolerable levels.

The designs of the component parts of the nebulizer are simple, facilitating easy manufacture and assembly: in fact the parts are so simple that inexpensive injection molding techniques may be employed. The designs enable the use of materials such as polycarbonate, which lend a further advantage as being washable and rendering the unit reusable.

It should be appreciated that the compact design of the manifold facilitates its ready shielding by lead to minimize the hazards extant in the use of radioactive pharmaceuticals. The compact design also saves on medicine as less medicine is wasted in the use of applicant's nebulizer. An additional facility enabling loading of the nebulizer from the top through the roof, further minimizes the loss of the pharmaceuticals.

BRIEF DESCRIPTION OF THE DRAWINGS

These and other objects, features and advantages of the invention will become apparent from a reading of the following specification when considered with the appended drawings wherein:

FIG. 1 is a side view of a manifold/nebulizer assembly constructed according to the invention, and including applicant's novel manifold and nebulizer, as well as a standard biological filter at the manifold exhaust port;

FIG. 2 is a side view of the manifold of FIG. 1, partially cut away to show the open check valve for the upper or intake chamber;

FIG. 3 is a similar view to FIG. 2, but showing a check valve open for fluid flow in the lower or exhaust chamber of the manifold;

FIG. 4 is a side view of the nebulizer of FIG. 1, showing the aerosol outlet port;

FIG. 5 is a cross-sectional view of the nebulizer of FIG. 4, taken along the section line 5—5; and FIG. 6 is an exploded view of the nebulizer of FIGS. 4 and 5.

DETAILED DESCRIPTION OF A PREFERRED EMBODIMENT OF THE INVENTION

As best shown in FIGS. 1, 2, and 3 of the drawings, a manifold, generally indicated by the numeral 10, includes a body 12 having tapered end portions 14 and 16 connected to tubes 18 and 20 respectively. Tubes 18 and 20 are of conventional or standard size facilitating the attachment of mouthpieces or hoses at one end and standard biological filters 22 at the other end. Body 12 of the manifold is divided into an upper and a lower, vertically juxtaposed, chamber or compartment by a horizontal member 24 extending the length of the body 12. The right hand end of the horizontal member 24 terminates against an end wall 26. The end wall 26 has openings 27 formed in it for permitting the passage of air in an inward direction for the upper chamber and in an outward direction for the lower chamber when check valves consisting of movable flaps 28 and 30 respectively are deflected by fluid pressure differences. FIG. 2 shows the check valve 28 being deflected inwardly upon the occurrence of a lower than atmospheric pressure in the upper chamber due to inhalation activity by the patient. FIG. 3 shows the check valve 30 for the lower chamber being deflected outward upon a higher than atmospheric pressure in the lower chamber due to exhalation activity by the patient.

The left hand ends of the upper and lower chambers in the manifold are both open to the tube 18. Spent air simply does not flow into the upper chamber on exhalation because the check valve 28 is closed. Likewise exhaled air in the lower chamber does not flow back towards the patient on inhalation because the lower check valve 30 then is closed; rather only medicated air in the upper chamber does, which was fresh air that entered the upper chamber on opening of the check valve 28 and flowed past the misting nebulizer.

The body 12 of the manifold 10 mounts the nebulizer generally midway of its length. As best seen in FIG. 1, the nebulizer, generally indicated by the numeral 32, extends through both the top and bottom of the body 12. The main body 34 of the nebulizer is tubular and of such size as to allow fresh air in the upper chamber to flow past it. The nebulizer extends downward through the horizontal member 24 to where it tapers to a reduced tubular portion 36 from which a gas nozzle 38 extends through the bottom of the body for connection to a hose attached at its other end to a suitable supply of gas under pressure.

As shown in FIG. 4, one side of the nebulizer includes an outlet opening or port 42, and the nebulizer is so mounted that the port 42 is located on the down stream side of the upper chamber. Air entering the right hand end of the upper chamber of the manifold is mixed with the nebulized medication (mist) from the nebulizer and exits through the manifold outlet opening or port 18 under the suction pressure of the patient during inhalation. The medicated air would be drawn into the patient either through a mouthpiece mounted directly on the tube 18 or through a hose (neither shown).

As best seen in FIGS. 5 and 6, the nebulizer 32 includes a passageway 44 for transmitting gas under pressure from the nozzle 38 to the flat upper end or surface 46 of a stem 48 projecting upwardly from the reduced tubular body portion 36. Above the flat upper end of the stem 48 is an orifice plate 50 whose orifice 52 is lined-up with the passageway 44 in the stem 48. The orifice plate 50 is urged away from the stem flat end or surface 46 to a spaced relationship therewith by a compression spring 54 seated on the tubular body portion 36 about the stem 48 and engaging the underside of the orifice plate 50. The compression spring 54 also surrounds a tube 56 depending from the orifice plate and surrounding the stem 48. The distance between the exterior surface of the stem 48 and the interior surface of the depending tube 56 is such that a liquid in the bottom of the nebulizer can be sucked upwards in the space between them, and laterally inward between the stem surface 46 and the lower surface of the orifice plate 50 because the space therebetween, by the aspirating action at the orifice. Gas under pressure in the passageway 44 will be jetted upwards through the layer of aspirated liquid to entrain liquid portions, and upwards through the orifice 52 to strike a rounded surface 58 on the lower end of a boss 60 from a depending plate 62 slidably mounted in the upper end of the nebulizer, and nebulize (mist) the entrained liquid portions. The orifice plate 50 is held in spaced relation to the boss plate 62 by a tube 64 extending upwards to where it engages the underside of the boss plate 62. Thus the compression spring 54 acting on the underside of the orifice plate 50 urges it upwards until its tube 64 engages the underside of the boss plate 62. It will be evident that the orifice plate 50 will therefore follow the position of the boss plate 62. It should also be observed that the upper end of the orifice plate tubular member 64 has cut-away portions 66 seen in FIG. 6 facilitating the exit of mist into the area about the orifice-plate tubular member 64 and a tube 68 depending from the boss plate 62. The aerosol mist is then directed downward around the boss plate tube 68 and up between boss plate tube 68 and the outer housing of the nebulizer 40 to where it exits through port 42 into the upper chamber of the manifold, for mixing with fresh air.

It should be further evident that the position of the orifice plate 50 with respect to the flat upper end of the passageway stem 48 is controlled by the position of the boss plate 62 under the influence of the compression spring 54. It should be likewise evident that the position of the boss plate 62 is determined by the position of a screw 70 threadedly mounted in the cap 72 of the nebulizer. The screw 70 is attached to an index knob 74 which facilitates turning of the screw to force the boss plate 62 and orifice plate 50 downwards to limit the amount of liquid being moved by means of aspiration to the area of the orifice 52, or to allow them to move upwards under the influence of the compression spring 54 to allow more fluid to enter the orifice area and therefore heavier aerosolization or misting.

The screw being threadedly received in the flat top 72 of the nebulizer, necessitates that the top be appropriately secured to the sidewall of the nebulizer.

Fluid is inserted into the body cavity of the nebulizer through an opening 76 in the cap.

In use, medication would be inserted into the nebulizer 32 via the opening 76. Gas under pressure would then be admitted to the passageway 44. The patient would then inhale, causing air to enter the upper chamber past the check valve 26. Gas under pressure from the passageway 44 would be jetting upwards and entraining the liquid medication that would have moved by aspiration to the vicinity of the orifice 52 in the orifice plate 50, and moving upwards through the orifice 52 to strike against the rounded end or surface 58 of the boss 60 to aerosolize the liquid medication. The resulting mist created flows outwards through the cut-away portions 66 in the upper end of the orifice-plate upwardly-extending tube 64 and downwards inside the boss-plate depending tube 68, then upwards between the boss plate depending tube 68 and the housing of the nebulizer 32 to exit through the output port 42. The air/aerosol mixture would continue through the upper chamber of the manifold and exit to the patient through the output port in the upper manifold tube 18.

If the mixture being absorbed by the patient was uncomfortable or of an inappropriate strength, suitable turning would be made of the index knob 74 on the nebulizer to vary the spacing between the stem surface 46 and the underside of the orifice plate to change the rate of aspiration.

It will be appreciated that the applicant has devised a compact nebulizer, one wherein the nebulizer is an integral portion of the manifold, and one that through an innovative valving mechanism lessens the re-circulation of the medicating liquid which results in less foaming and better use of the medication and even in the use of less medication. On the other hand, safety is facilitated by the fact that the compact design allows lead shielding of a handable weight to be employed in the case of nuclear medicine amplications. Improved control of liquid flow in the nebulizer results in less aeration and foaming of the medication. Since less air volumes are used, less gas supplies are required, enabling the use of portable air supplies. In fact, the system that the applicant has designed lends itself to home use most effectively.

The simplicity of the design lends itself to easy manufacture and assembly. Even materials, such as polycarbonate materials which are reuseable, can be used to inexpensively injection mold the simple parts.

While applicant has shown and described a preferred embodiment of the invention, it will be apparent to those skilled in the art that other embodiments utilizing principles of the invention can be readily fabricated. Accordingly it is intended to be limited only by the scope or spirit of the appended claims.

What is claimed is:

1. An aerosol delivery system comprising an elongated tubular housing defined by an outer wall and having an interior transverse member dividing said housing into first and second elongated chambers terminating in common first and second ends; valve means located at said first common end to permit opposed one-way flows through said first and second chambers; and nebulizer means having a housing extending through said first and second chambers and having an exit port positioned within one of said first and second chambers whereby an airflow through said one of said first and second chambers draws nebulous fluid from said nebulizer means exit port into said airflow for delivery from said tubular housing.

2. The delivery system according to claim 1, wherein said nebulizer comprises a fixed stem extending within said housing and a tube terminating in an orifice plate concentric with said stem to define a liquid passageway therebetween, said orifice plate being adjustable with respect to a top surface of said fixed stem to control the fluid flow therebetween.

3. The apparatus according to claim 2, wherein said nebulizer further comprises a spring mounted and adapted to bias said orifice plate away from said top surface of said fixed stem.

4. The apparatus of claim 3, wherein said nebulizer further comprises a moveable element having a depending boss with a rounded lower end adapted to be struck by a jet stream entraining liquid to produce fine particles.

5. The apparatus of claim 4, wherein said orifice plate comprises a portion of said moveable element.

* * * * *